United States Patent
van der Burg et al.

(10) Patent No.: US 6,352,553 B1
(45) Date of Patent: *Mar. 5, 2002

(54) STENT-GRAFT DEPLOYMENT APPARATUS AND METHOD

(75) Inventors: Erik van der Burg, Sunnyvale; Eric Leopold, San Jose; Ramiro Reyes, Union City, all of CA (US)

(73) Assignee: Gore Enterprise Holdings, Inc., Newark, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/896,804

(22) Filed: Jul. 18, 1997

Related U.S. Application Data

(63) Continuation of application No. 08/620,273, filed on Mar. 22, 1996, now abandoned, which is a continuation-in-part of application No. 08/572,436, filed on Dec. 14, 1995, now abandoned.

(51) Int. Cl.[7] .................................................. A61F 2/00
(52) U.S. Cl. ....................................................... 623/1.23
(58) Field of Search ................................. 623/1, 11, 12, 623/1.11, 1.23; 606/108, 191, 194, 195, 198

(56) References Cited

U.S. PATENT DOCUMENTS

| | | | |
|---|---|---|---|
| 2,638,093 A | 5/1953 | Kulick | |
| 3,029,819 A | 4/1962 | Starks | |
| 3,096,560 A | 7/1963 | Liebig | |
| 3,142,067 A | 7/1964 | Liebig | |
| 3,152,618 A | 10/1964 | Rothermel et al. | |

(List continued on next page.)

FOREIGN PATENT DOCUMENTS

| | | |
|---|---|---|
| AU | 42485/89 | 4/1990 |
| AU | 34742/93 | 1/1993 |
| CA | 2026604 | 4/1991 |
| CA | 2079417 | 4/1993 |
| DE | 37 24 514 A1 | 2/1989 |

(List continued on next page.)

OTHER PUBLICATIONS

Cragg, "Percutaneous Femoropopliteal Graft Placement" *Radiology* (1993) 187 (3):643–648.

Hagen et al, "Self–Expandable Macroporous Nitinol Stents for Transfemoral Exclusion of Aortic Aneurysms in Dogs: Preliminary Results" *Cardiovascular Intervention Radiology* (1993) 16:339–342.

Cragg, et al.; Percutaneous Femoropopliteal Graft Placement; *Journal of Vascular and Interventional Radiology*; pp. 455–462; Jul.–Aug. 1993; vol. 4, No. 4.

Cragg et al. Nitinol Intravascular Stent: Results of Preclinical Evaluation: *Radiology*; pp. 775–778; Dec. 1993; vol. 189, No. 3.

(List continued on next page.)

*Primary Examiner*—Michael J. Milano
(74) *Attorney, Agent, or Firm*—Morgan & Finnegan, LLP

(57) ABSTRACT

A stent or stent-graft deployment apparatus or mechanism configured so that, when activated, the stent or stent-graft progressively expands in a direction from its end which is proximally positioned to the deployment instrument, such as a percutaneous catheter, to its end which is distally positioned to the deployment instrument. The stent or stent-graft deployment mechanism includes a tether or slip line configuration which reduces the likelihood of snagging between the line and stent member. A method is also provided for deploying a stent or stent-graft within a mammalian lumen which includes expanding the stent or stent-graft in such a proximal-to-distal direction. The apparatus and method of the present invention minimize the likelihood of the stent or stent-graft from being displaced from the desired site before it is somewhat secured in the vessel during deployment.

20 Claims, 3 Drawing Sheets

U.S. PATENT DOCUMENTS

| | | |
|---|---|---|
| 3,174,851 A | 3/1965 | Buchler et al. |
| 3,351,463 A | 11/1967 | Rozner et al. |
| 3,479,670 A | 11/1969 | Medell |
| 3,514,791 A | 6/1970 | Sparks |
| 3,562,820 A | 2/1971 | Braun |
| 3,625,198 A | 12/1971 | Sparks |
| 3,657,744 A | 4/1972 | Ersek |
| 3,710,777 A | 1/1973 | Sparks |
| 3,753,700 A | 8/1973 | Harrison et al. |
| 3,774,596 A | 11/1973 | Cook |
| 3,805,301 A | 4/1974 | Liebig |
| 3,866,247 A | 2/1975 | Sparks |
| 3,866,609 A | 2/1975 | Sparks |
| 3,868,956 A | 3/1975 | Alfidi et al. |
| 3,927,422 A | 12/1975 | Sawyer |
| 3,938,524 A | 2/1976 | Sparks, deceased et al. |
| 3,949,073 A | 4/1976 | Daniels et al. |
| 3,953,566 A | 4/1976 | Gore |
| 3,974,526 A | 8/1976 | Dardik et al. |
| 3,993,045 A | 11/1976 | Ion |
| 4,011,861 A | 3/1977 | Enger |
| 4,047,252 A | 9/1977 | Liebig et al. |
| 4,130,904 A | 12/1978 | Whalen |
| 4,140,126 A | 2/1979 | Choudhury |
| 4,164,045 A | 8/1979 | Bokros et al. |
| 4,187,390 A | 2/1980 | Gore |
| 4,300,244 A | 11/1981 | Bokros |
| 4,306,318 A | 12/1981 | Mano et al. |
| 4,319,363 A | 3/1982 | Ketharanathan |
| 4,355,426 A | 10/1982 | MacGregor |
| 4,411,655 A | 10/1983 | Schreck |
| 4,424,208 A | 1/1984 | Wallace et al. |
| 4,425,908 A | 1/1984 | Simon |
| 4,488,911 A | 12/1984 | Luck et al. |
| 4,494,531 A | 1/1985 | Gianturco |
| 4,502,159 A | 3/1985 | Woodroof et al. |
| 4,503,569 A | 3/1985 | Dotter |
| 4,512,338 A | 4/1985 | Balko et al. |
| 4,517,687 A | 5/1985 | Liebig et al. |
| 4,530,113 A | 7/1985 | Matterson |
| 4,546,500 A | 10/1985 | Bell |
| 4,553,545 A | 11/1985 | Maass et al. |
| 4,557,764 A | 12/1985 | Chu |
| 4,562,596 A | 1/1986 | Kornberg |
| 4,580,568 A | 4/1986 | Gianturco |
| 4,582,640 A | 4/1986 | Smestad et al. |
| 4,592,754 A | 6/1986 | Gupte et al. |
| 4,604,762 A | 8/1986 | Robinson |
| 4,617,932 A | 10/1986 | Kornberg |
| 4,629,458 A | 12/1986 | Pinchuk |
| 4,641,653 A | 2/1987 | Rockey |
| 4,642,117 A | 2/1987 | Nguyen et al. |
| 4,647,416 A | 3/1987 | Seiler, Jr. et al. |
| 4,649,922 A | 3/1987 | Wiktor |
| 4,655,771 A | 4/1987 | Wallsten |
| 4,665,906 A | 5/1987 | Jervis |
| 4,689,399 A | 8/1987 | Chu |
| 4,728,328 A | 3/1988 | Hughes et al. |
| 4,733,665 A | 3/1988 | Palmaz |
| 4,738,666 A | 4/1988 | Fuqua |
| 4,739,762 A | 4/1988 | Palmaz |
| 4,740,207 A | 4/1988 | Kreamer |
| 4,760,849 A | 8/1988 | Kropf |
| 4,776,337 A | 10/1988 | Palmaz |
| 4,787,899 A | 11/1988 | Lazarus |
| 4,790,313 A | 12/1988 | Borrelly |
| 4,795,458 A | 1/1989 | Regan |
| 4,798,606 A | 1/1989 | Pinchuk |
| 4,800,882 A | 1/1989 | Gianturco |
| 4,816,028 A | 3/1989 | Kapadia et al. |
| 4,816,339 A | 3/1989 | Tu et al. |
| 4,820,298 A | 4/1989 | Leveen et al. |
| 4,830,003 A | 5/1989 | Wolff et al. |
| 4,842,575 A | 6/1989 | Hoffman, Jr. et al. |
| 4,856,516 A | 8/1989 | Hillstead |
| 4,877,025 A | 10/1989 | Hanson |
| 4,878,906 A | 11/1989 | Lindemann et al. |
| 4,886,062 A | 12/1989 | Wiktor |
| 4,886,500 A | 12/1989 | Lazarus |
| 4,892,539 A | 1/1990 | Koch |
| 4,913,141 A * | 4/1990 | Hillstead .................... 606/198 |
| 4,921,479 A | 5/1990 | Grayzel |
| 4,941,870 A | 7/1990 | Okada et al. |
| 4,950,227 A | 8/1990 | Savin et al. |
| 4,955,899 A | 9/1990 | Corna et al. |
| 4,957,504 A | 9/1990 | Chardack |
| 4,957,508 A | 9/1990 | Kaneko et al. |
| 4,969,458 A | 11/1990 | Wiktor |
| 4,990,151 A | 2/1991 | Wallsten |
| 4,990,155 A | 2/1991 | Wilkoff |
| 4,994,071 A | 2/1991 | MacGregor |
| 5,007,926 A | 4/1991 | Derbyshire |
| 5,015,253 A | 5/1991 | MacGregor |
| 5,019,085 A * | 5/1991 | Hillstead .................... 606/198 |
| 5,019,090 A | 5/1991 | Pinchuk |
| 5,035,706 A * | 7/1991 | Giantureo et al. .......... 606/198 |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,042,161 A | 8/1991 | Hodge |
| 5,064,435 A | 11/1991 | Porter |
| 5,066,298 A * | 11/1991 | Hess .......................... 606/194 |
| 5,067,957 A | 11/1991 | Jervis |
| 5,078,726 A | 1/1992 | Kreamer |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,424 A | 4/1992 | Hoffman, Jr. et al. |
| 5,122,154 A | 6/1992 | Rhodes |
| 5,123,917 A | 6/1992 | Lee |
| 5,127,919 A | 7/1992 | Ibrahim et al. |
| 5,133,732 A | 7/1992 | Wiktor |
| 5,139,480 A | 8/1992 | Hickle et al. |
| 5,147,370 A | 9/1992 | McNamara et al. |
| 5,151,105 A | 9/1992 | Kwan-Gett |
| 5,156,619 A | 10/1992 | Ehrenfeld |
| 5,161,547 A | 11/1992 | Tower |
| 5,162,430 A | 11/1992 | Rhee et al. |
| 5,163,958 A | 11/1992 | Pinchuk |
| 5,171,262 A | 12/1992 | MacGregor |
| 5,178,630 A | 1/1993 | Schmitt |
| 5,192,289 A | 3/1993 | Jessen |
| 5,192,307 A | 3/1993 | Wall |
| 5,195,984 A | 3/1993 | Schatz |
| 5,197,977 A | 3/1993 | Hoffman, Jr. et al. |
| 5,197,978 A | 3/1993 | Hess |
| 5,201,757 A | 4/1993 | Heyn et al. |
| 5,209,735 A | 5/1993 | Lazarus |
| 5,211,658 A | 5/1993 | Clouse |
| 5,213,580 A | 5/1993 | Slepian et al. |
| 5,217,483 A | 6/1993 | Tower |
| 5,221,261 A | 6/1993 | Termin et al. |
| 5,226,913 A | 7/1993 | Pinchuk |
| 5,232,446 A | 8/1993 | Arney |
| 5,236,447 A | 8/1993 | Kubo et al. |
| 5,242,451 A | 9/1993 | Harada et al. |
| 5,246,452 A | 9/1993 | Sinnott |
| 5,258,042 A | 11/1993 | Mehta |
| 5,264,276 A | 11/1993 | McGregor et al. |

| Patent | Date | Inventor |
|---|---|---|
| 5,271,410 A | 12/1993 | Wolzinger et al. |
| 5,276,276 A | 1/1994 | Gunn |
| 5,282,824 A | 2/1994 | Gianturco |
| 5,282,846 A | 2/1994 | Schmitt |
| 5,282,847 A | 2/1994 | Trescony et al. |
| 5,282,848 A | 2/1994 | Schmitt |
| 5,290,305 A | 3/1994 | Inoue |
| 5,306,261 A | 4/1994 | Alliger et al. |
| 5,306,294 A | 4/1994 | Winston et al. |
| 5,314,472 A | 5/1994 | Fontaine |
| 5,324,304 A | 6/1994 | Rasmussen |
| 5,324,323 A | 6/1994 | Bui |
| 5,330,528 A | 7/1994 | Lazim |
| 5,336,254 A | 8/1994 | Brennen et al. |
| 5,342,348 A | 8/1994 | Kaplan |
| 5,342,387 A | 8/1994 | Summers |
| 5,344,426 A | 9/1994 | Lau et al. |
| 5,348,537 A | 9/1994 | Wiesner et al. |
| 5,354,308 A | 10/1994 | Simon et al. |
| 5,354,309 A | 10/1994 | Schnepp-Pesch et al. |
| 5,356,423 A | 10/1994 | Tihon et al. |
| 5,360,443 A | 11/1994 | Barone et al. |
| 5,366,472 A | 11/1994 | Hillstead |
| 5,366,473 A | 11/1994 | Winston et al. |
| 5,366,504 A | 11/1994 | Andersen et al. |
| 5,370,691 A | 12/1994 | Samson |
| 5,372,600 A | 12/1994 | Beyar et al. |
| 5,382,261 A | 1/1995 | Palmaz |
| 5,383,928 A | 1/1995 | Scott et al. |
| 5,385,580 A | 1/1995 | Schmitt |
| 5,387,235 A | 2/1995 | Chuter |
| 5,405,377 A * | 4/1995 | Cragg .................. 606/198 |
| 5,405,378 A | 4/1995 | Strecker |
| 5,413,598 A | 5/1995 | Moreland |
| 5,421,955 A | 6/1995 | Lau et al. |
| 5,423,849 A | 6/1995 | Eugelson et al. |
| 5,425,710 A | 6/1995 | Kahir et al. |
| 5,425,739 A | 6/1995 | Jessen |
| 5,443,500 A | 8/1995 | Sigwart |
| 5,449,373 A | 9/1995 | Pinchasik et al. |
| 5,453,084 A | 9/1995 | Moses |
| 5,456,713 A | 10/1995 | Chuter |
| 5,456,721 A | 10/1995 | Legrand |
| 5,458,605 A | 10/1995 | Klemm |
| 5,458,615 A | 10/1995 | Klemm et al. |
| 5,464,449 A | 11/1995 | Ryan et al. |
| 5,476,506 A | 12/1995 | Lunn |
| 5,480,423 A | 1/1996 | Ravenscroft et al. |
| 5,484,444 A | 1/1996 | Braudschweiler |
| 5,487,858 A | 1/1996 | Schmitt |
| 5,489,295 A | 2/1996 | Piplani et al. |
| 5,496,364 A | 3/1996 | Schmitt |
| 5,496,365 A | 3/1996 | Sgro |
| 5,499,994 A | 3/1996 | Tihon et al. |
| 5,507,767 A | 4/1996 | Maeda et al. |
| 5,507,769 A | 4/1996 | Marin et al. |
| 5,507,771 A | 4/1996 | Gianturco |
| 5,509,902 A | 4/1996 | Raulerson |
| 5,509,931 A | 4/1996 | Schmitt |
| 5,514,154 A | 5/1996 | Lau et al. |
| 5,522,822 A | 6/1996 | Phelps et al. |
| 5,522,880 A | 6/1996 | Barone et al. |
| 5,522,881 A | 6/1996 | Lentz |
| 5,522,961 A | 6/1996 | Leonhardt |
| 5,540,701 A * | 7/1996 | Sharkey et al. ............. 623/1 |
| 5,540,712 A | 7/1996 | Kleshinski et al. |
| 5,545,210 A | 8/1996 | Hess et al. |
| 5,545,211 A | 8/1996 | An et al. |
| 5,549,635 A | 8/1996 | Solar |
| 5,549,663 A * | 8/1996 | Cottone, Jr. ............. 623/1 |
| 5,554,180 A | 9/1996 | Turk |
| 5,554,181 A | 9/1996 | Das |
| 5,554,182 A | 9/1996 | Dinh et al. |
| 5,556,413 A | 9/1996 | Lam |
| 5,562,724 A | 10/1996 | Vorwerk et al. |
| 5,562,726 A | 10/1996 | Chuter |
| 5,562,727 A | 10/1996 | Turk et al. |
| 5,571,166 A | 11/1996 | Dinh et al. |
| 5,571,169 A | 11/1996 | Plaia et al. |
| 5,571,172 A | 11/1996 | Chin |
| 5,571,173 A | 11/1996 | Parodi |
| 5,571,176 A | 11/1996 | Taheri |
| 5,575,815 A | 11/1996 | Slepian et al. |
| 5,575,816 A | 11/1996 | Rudnick et al. |
| 5,575,817 A | 11/1996 | Martin |
| 5,578,071 A | 11/1996 | Parodi |
| 5,591,197 A | 1/1997 | Orth et al. |
| 5,591,198 A | 1/1997 | Boyle et al. |
| 5,591,228 A | 1/1997 | Edoga |
| 5,591,229 A | 1/1997 | Parodi |
| 5,599,305 A | 2/1997 | Hermann et al. |
| 5,607,442 A | 3/1997 | Fischell et al. |
| 5,607,444 A | 3/1997 | Lam |
| 5,607,445 A | 3/1997 | Summers |
| 5,609,625 A | 3/1997 | Piplani et al. |
| 5,609,627 A | 3/1997 | Goicoechea et al. |
| 5,620,763 A | 4/1997 | House et al. |
| 5,622,188 A | 4/1997 | Plaia et al. |
| 5,626,561 A | 5/1997 | Butler et al. |
| 5,628,783 A | 5/1997 | Quiachon et al. |
| 5,628,784 A | 5/1997 | Strecker |
| 5,628,788 A | 5/1997 | Pinchuk |
| 5,632,763 A | 5/1997 | Glastra |
| 5,632,772 A | 5/1997 | Alcime et al. |
| 5,637,113 A | 6/1997 | Tartaglia et al. |
| 5,639,278 A | 6/1997 | Dereueme et al. |
| 5,643,208 A | 7/1997 | Parodi |
| 5,647,380 A | 7/1997 | Campbell et al. |
| 5,649,978 A | 7/1997 | Samson |
| 5,653,743 A | 8/1997 | Martin |
| 5,653,748 A | 8/1997 | Strecker |
| 5,662,614 A | 9/1997 | Edoga |
| 5,662,675 A | 9/1997 | Stockert et al. |
| 5,662,701 A | 9/1997 | Plaia et al. |
| 5,662,713 A | 9/1997 | Andersen et al. |
| 5,665,117 A | 9/1997 | Rhodes |
| 5,667,523 A | 9/1997 | Bynon et al. |
| 5,669,924 A | 9/1997 | Shaknovich |
| 5,669,930 A | 9/1997 | Igarashi |
| 5,674,276 A | 10/1997 | Andersen et al. |
| 5,676,671 A | 10/1997 | Inoue |
| 5,676,696 A | 10/1997 | Marcade |
| 5,676,697 A | 10/1997 | McDonald |
| 5,681,346 A | 10/1997 | Orth et al. |
| 5,683,449 A | 11/1997 | Marcade |
| 5,683,450 A | 11/1997 | Goicoechea et al. |
| 5,683,451 A | 11/1997 | Lenker et al. |
| 5,683,452 A | 11/1997 | Barone et al. |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,517 A | 12/1997 | Marin et al. |
| 5,697,970 A | 12/1997 | Schmitt et al. |
| 5,700,285 A | 12/1997 | Myers et al. |
| 5,700,286 A | 12/1997 | Taraglia |
| 5,709,657 A | 1/1998 | Zimmon |
| 5,713,917 A | 2/1998 | Leonhardt et al. |
| 5,716,365 A | 2/1998 | Goicoechea et al. |
| 5,718,724 A | 2/1998 | Goicoechea et al. |
| 5,718,973 A | 2/1998 | Lewis et al. |
| 5,720,776 A | 2/1998 | Chuter et al. |

| | | |
|---|---|---|
| 5,723,003 A | 3/1998 | Winston et al. |
| 5,723,004 A | 3/1998 | Dereume et al. |
| 5,728,131 A | 3/1998 | Frantzen et al. |
| 5,728,150 A | 3/1998 | McDonald et al. |
| 5,730,698 A | 3/1998 | Fischell et al. |
| 5,732,572 A | 3/1998 | Litton |
| 5,735,892 A | 4/1998 | Myers et al. |
| 5,741,274 A | 4/1998 | Lenker et al. |
| 5,741,325 A | 4/1998 | Chaikof et al. |
| 5,749,825 A | 5/1998 | Fischell et al. |
| 5,749,880 A | 5/1998 | Banas et al. |
| 5,749,921 A | 5/1998 | Lenker et al. |
| 5,755,769 A | 5/1998 | Richard et al. |
| 5,769,882 A | 6/1998 | Fogarty et al. |
| 5,779,732 A | 7/1998 | Amundson |
| 5,782,904 A | 7/1998 | White et al. |
| 5,800,521 A | 9/1998 | Orth |
| 5,800,522 A | 9/1998 | Campbell et al. |
| 5,800,524 A | 9/1998 | Borghi |
| 5,810,870 A | 9/1998 | Myers et al. |
| 5,824,041 A | 10/1998 | Lenker et al. |
| 5,843,069 A | 12/1998 | Butler et al. |
| 5,843,171 A | 12/1998 | Campbell et al. |
| 5,865,723 A | 2/1999 | Love |
| 5,868,704 A | 2/1999 | Campbell et al. |
| 5,873,906 A | 2/1999 | Lau et al. |
| 5,876,432 A | 3/1999 | Lau et al. |
| 5,888,243 A | 3/1999 | Silvestrini |
| 5,919,225 A | 7/1999 | Lau et al. |
| 5,925,061 A | 7/1999 | Ogi et al. |
| 5,925,075 A | 7/1999 | Myers et al. |
| 5,961,546 A | 10/1999 | Robinson et al. |
| 5,972,441 A | 10/1999 | Campbell et al. |
| 5,976,650 A | 11/1999 | Campbell et al. |
| 5,993,489 A | 11/1999 | Lewis et al. |
| 6,001,123 A | 12/1999 | Lau |
| 6,015,429 A | 1/2000 | Lau et al. |
| 6,015,431 A | 1/2000 | Thornton et al. |
| 6,017,362 A | 1/2000 | Lau |
| 6,019,787 A | 1/2000 | Richard et al. |
| 6,019,788 A | 1/2000 | Butters et al. |
| 6,025,044 A | 2/2000 | Campbell et al. |
| 6,027,779 A | 2/2000 | Campbell et al. |
| 6,027,811 A | 2/2000 | Campbell et al. |
| 6,042,605 A | 3/2000 | Martin et al. |
| 6,048,484 A | 4/2000 | House et al. |
| 6,086,604 A | 7/2000 | Fischell et al. |
| 6,120,477 A | 9/2000 | Campbell et al. |
| 6,139,572 A | 10/2000 | Campbell et al. |
| 6,159,565 A | 12/2000 | Campbell et al. |
| 6,165,210 A | 12/2000 | Lau et al. |
| 6,193,745 B1 | 2/2001 | Fogarty et al. |
| 6,203,568 B1 | 3/2001 | Lombardi et al. |

FOREIGN PATENT DOCUMENTS

| | | |
|---|---|---|
| DE | 39 18736 A1 | 12/1990 |
| DE | 41 37 857 A1 | 5/1992 |
| DE | 196 17 823 | 11/1997 |
| EP | 0 382 014 | 1/1990 |
| EP | 0 382 014 | 8/1990 |
| EP | 0 408 245 | 1/1991 |
| EP | 0 418 677 | 3/1991 |
| EP | 0 423 916 B1 | 4/1991 |
| EP | 0 435 518 A1 | 7/1991 |
| EP | 0 464 755 A1 | 1/1992 |
| EP | 0 472 731 | 3/1992 |
| EP | 0 540 290 | 5/1993 |
| EP | 0 551 179 A1 | 7/1993 |
| EP | 0 556 850 | 8/1993 |
| EP | 0 565 251 | 10/1993 |
| EP | 0 667 131 A2 | 1/1995 |
| EP | 0 689 806 A2 | 5/1995 |
| EP | 0 686 379 | 12/1995 |
| EP | 0 696 447 A2 | 2/1996 |
| EP | 0 701 800 A1 | 3/1996 |
| EP | 0 705 577 A1 | 4/1996 |
| EP | 0 716 834 A1 | 6/1996 |
| EP | 0 747 020 A2 | 12/1996 |
| FR | 2 678 508 | 8/1993 |
| GB | 1355373 | 5/1971 |
| GB | 1 506 432 | 5/1971 |
| GB | 1 567 122 | 3/1978 |
| GB | 1 506 432 | 4/1978 |
| GB | 1 567 122 | 5/1980 |
| GB | 1 355 373 | 6/1994 |
| JP | 02-174859 | 7/1990 |
| JP | 06-007454 | 1/1994 |
| JP | 06-181993 | 7/1994 |
| JP | 7-500272 T | 1/1995 |
| JP | 07-024688 | 3/1995 |
| JP | 8-509899 T | 10/1996 |
| SU | 1635980 A1 | 12/1988 |
| WO | WO 88/06026 | 8/1988 |
| WO | WO 90/04982 | 5/1990 |
| WO | WO 92/03107 | 3/1992 |
| WO | WO 92/04097 | 3/1992 |
| WO | WO 92/06734 | 4/1992 |
| WO | WO 92/09246 | 6/1992 |
| WO | WO 93/13825 | 7/1993 |
| WO | WO 93/17636 | 9/1993 |
| WO | WO 93/19803 | 10/1993 |
| WO | WO 93/19804 | 10/1993 |
| WO | WO 93/22984 | 11/1993 |
| WO | WO 93/22986 | 11/1993 |
| WO | WO 93/22989 | 11/1993 |
| WO | WO 94/00179 | 1/1994 |
| WO | WO 94/01483 | 1/1994 |
| WO | WO 94/04097 | 3/1994 |
| WO | WO 94/12136 | 6/1994 |
| WO | WO 94/15549 | 7/1994 |
| WO | WO 95/01466 | 2/1995 |
| WO | WO 95/05131 | 2/1995 |
| WO | WO 95/05132 | 2/1995 |
| WO | WO 95/09586 | 4/1995 |
| WO | WO 95/21592 | 8/1995 |
| WO | WO 95/26695 | 10/1995 |
| WO | WO 96/10967 | 4/1996 |
| WO | WO 96/18360 | 6/1996 |
| WO | WO 96/18361 | 6/1996 |
| WO | WO 96/24306 | 8/1996 |
| WO | WO 97/21402 | 6/1997 |
| WO | WO 97/21403 | 6/1997 |
| WO | WO 97/21641 | 6/1997 |
| WO | WO 98/30173 | 7/1998 |

OTHER PUBLICATIONS

Laborde et al., "Intraluminal Bypass of Abdominal Aortic Aneurysm: Feasibility Study"; *Radiology* 1992, 184:185–190.

Product Brochure for Cook–Z™ Stents, Gianturco–Rösch Biliary Design, Cook©, A Cook Groups Company, P.O. Box 489, Bloomington, IN, 47402, U.S.A., 4 pages total, (1989).

MinTec™ Minimally Invasive Technologies Product Brochure for the Craggstent and Cragg EndoPro System 1, 4 pages total.

Blum, U. et al.; "Dacron Endografts for Infrarenal Abdominal Aortic Aneurysms: 2 Year Follow–Up"; Fifth international and Interdisciplinary Symposium on Endoluminal Stents and Grafts (Oct. 10–13, 1996) Washington, D.C., 2 pages total.

Chuter et al.; "Bifurcated stent–grafts for AAA: 3 year follow–up"; Abstracts from the Seventh International Course on Peripheral Vascular Intervention; J. Endovas. Surg. (1996) 3:453.

Chuter et al.; "Bifurcated stent–grafts for AAA: 3 year follow–up"; *Fifth International and Interdisciplinary Symposium on Endoluminal Stents and Grafts* (Oct. 10–13, 1996) Washington, D.C., 2 pages total.

Dereume, JP et al.; "Endoluminal Treatment Of Abdominal Aortic Aneurysm with the Corvita Endovascular Graft, Results of a Single–Center, Prospective Feasibility Study of 90 Patients"; *Abstracts from the Seventh International Course on Peripheral Vascular Intervention* J. Endovasc. Surg. (1996) 3:460–461.

Katzen et al., "initial experience performing combined surgical/interventional procedures in the interventiona suite" *Abstracts from the Seventh International Course on Peripheral Vascular Intervention J. Endovasc. Surg.* (1996) 3:467.

Moore et al., "Transfemoral endovascular repair of abdominal aortic aneurysm: Result of the North American EVT phase 1 trial" J. Vasc. Surg. (1996) 23:543–552.

Parodi et al., "long–term follow–up of AAA endoluminal repair" Abstracts from the Seventh International Course on Peripheral Vascular Intervention. J. Endovasc. Surg. (1996) 3:3335.

Product Brochure for Catheters, Guidewires, and Stents (no date) Schneider (USA) Inc., Pfizer Hospital Products Group, 5905 Nathan Lane, Minneapolis, Minnesota, 55442.

Product Brochure for *PalmazTM* Balloon–Expandable Stent, Johnson & Johnson Interventional Systems, 40 Technology Drive, P.O. Box 4917, Warren, NJ, 07059, 2 pages total, (1990).

White et al., "Endoleak following endoluminal repair of AAA: Diagnosis, significance, and amanagement" *Abstracts from the Seventh International Course on Peripheral Vascular Intervention J. Endovasc. Surg.* (1996) 3:339–340.

Wilson et al.; "A self expanding bifurcated endovascular graft for Abdominal Aortic Aneurysm Repair. An Initial Study in a Canine Model" ASAIO Journal 42(5): 386–393 (1996).

World Medical News, World Medical manufacturing Corporation, 13794 NW 4th Street, Bldgs. 210 & 211, Sunrise, Florida, 33325 U.S.A., vol. 5, Issue 3 (July 1996) 3 pages total.

U.S. application No. 08/772,372, Thorton, et al., filed Dec. 23, 1996, pending.

U.S. application No. 08772/373, Leopold, et al., filed Dec. 23, 1996, pending.

U.S. application No. 08/871,427, Lau, et al., filed Jun. 9, 1997, pending.

U.S. application No. 08/896,373, Lau, et al., filed Aug. 18, 1997, pending.

U.S. application No. 08/903,210, Lau, et al., filed Jul. 21, 1997, pending.

U.S. application No. 09/207,944, Vonesh et al., filed Dec. 9, 1998, response.

U.S. application No. 09/235,214, Brauker et al., filed Jan. 22, 1999.

U.S. application No. 09/235,458, Vonesh et al., filed Jan. 22, 1999, response.

U.S. application No. 09/306,522, Myers, filed May 6, 1999.

U.S. application No. 09/376,931, Martin, et al., filed Aug. 13, 1999, pending.

U.S. application No. 09/408,866, Brenton et al., filed Sep. 30, 1999, response.

U.S. application No. 09/488,229, Cully et al., filed Jan. 20, 2000.

U.S. application No. 09/489,604, Vonesh et al., filed Jan. 20, 2000.

U.S. application No. 09/510,937, Goffena et al., filed Feb. 22, 2000, response.

* cited by examiner

STENT-GRAFT DEPLOYMENT APPARATUS AND METHOD

This is a continuation of application Ser. No. 08/620,273, filed on Mar. 22, 1996, now abandoned, which is a continuation-in-part application for application Ser. No. 08/572,436, entitled Stent-Graft Deployment Apparatus and Method, filed on Dec. 14, 1995, now abandoned.

BACKGROUND OF THE INVENTION

This invention relates generally to implants for repairing ducts and passageways in the body. More specifically, the invention relates to an apparatus and procedures for deploying a stent-graft in mammalian vasculature.

A variety of stent or stent-graft designs and deployment mechanisms have been developed. For various reasons, many of these stent-grafts tend to become displaced from the intended deployment site within a lumen upon deployment prior to being secured within the lumen. Thus, there is a need to improve stent or stent-graft deployment placement accuracy and reliability within a vessel. Additionally, there exists a need to improve upon the reliability of the devices used for deployment of the stent-grafts.

SUMMARY OF THE INVENTION

The present invention involves medical devices and method(s) for deploying an expandable stent or stent-graft within mammalian lumens. According to the present invention, a medical device comprises a stent (or stent-graft) which has a proximal portion and a distal portion, and means for progressively deploying or expanding the stent, preferably a tether or slip line, which is releaseably coupled to the stent. The line is arranged such that when it is released from the stent, the stent progressively expands in a direction from its proximal portion to its distal portion. In order to accomplish progressive expansion of the stent, according to one variation of the slip-line embodiment the line is preferably arranged in a sack knot configuration. According to a further aspect of the slip line embodiment, the line has a fixed end associated with the distal portion of the stent and a release end associated with the proximal portion of the stent. The release end of the line is pullable to actuate expansion of the stent.

The position of the line and the sack knot configuration can eliminate the need for doubling back the line to minimize the risk of snagging between the line and the stent device, thus, increasing deployment reliability. According to another aspect of the present invention, the stent or stent-graft described above may be placed within a lumen from a direction against the flow of fluid (e.g., blood). The stent expands or unfolds in a direction from its downstream end to its upstream end relative to the fluid flow. Thus, the present invention may minimize the likelihood of the device being displaced from the desired site before it is somewhat secured in the vessel during deployment.

According to another aspect of the invention, a delivery member, such as a catheter or guide wire, may be used to place the stent or stent-graft at the intended delivery site. When used with a catheter, the stent is releasably coupled, as described above, adjacent to the catheter's shaft portion, with the stent's proximal end being adjacent to the distal end of the catheter's shaft portion.

A preferred method of the present invention involves placing a folded stent device attached to a stent delivery member, such as a catheter, at a desired site within a mammalian lumen, and then progressively unfolding the stent device in a direction away from the stent delivery member.

The above is a brief description of some deficiencies in the prior art and advantages of the present invention. Other features, advantages, and embodiments of the invention will be apparent to those skilled in the art from the following description, accompanying drawings and appended claims.

DETAILED DESCRIPTION OF THE INVENTION

Figure 2:
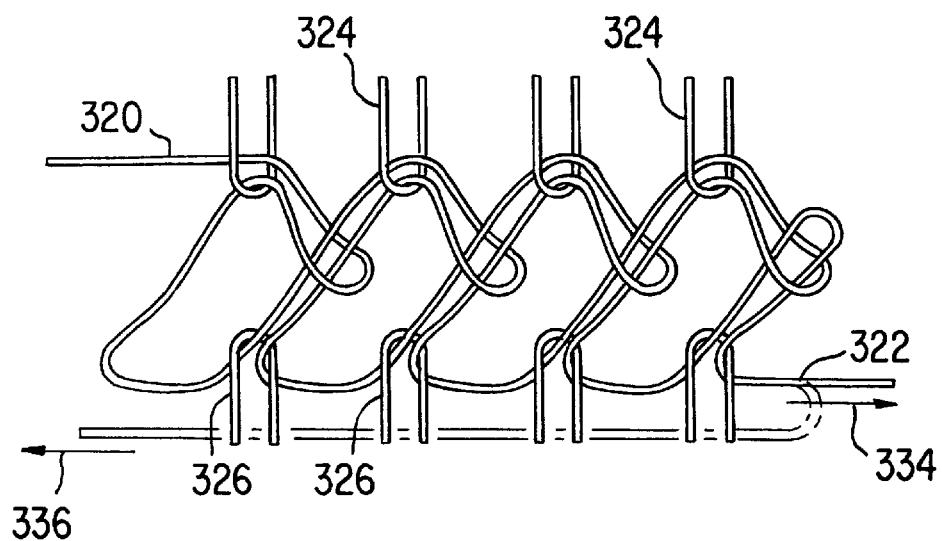
FIG. 2 shows an enlarged view of a stent fold line using the tether line in the sack knot configuration of FIG. 1.
Figure 1:
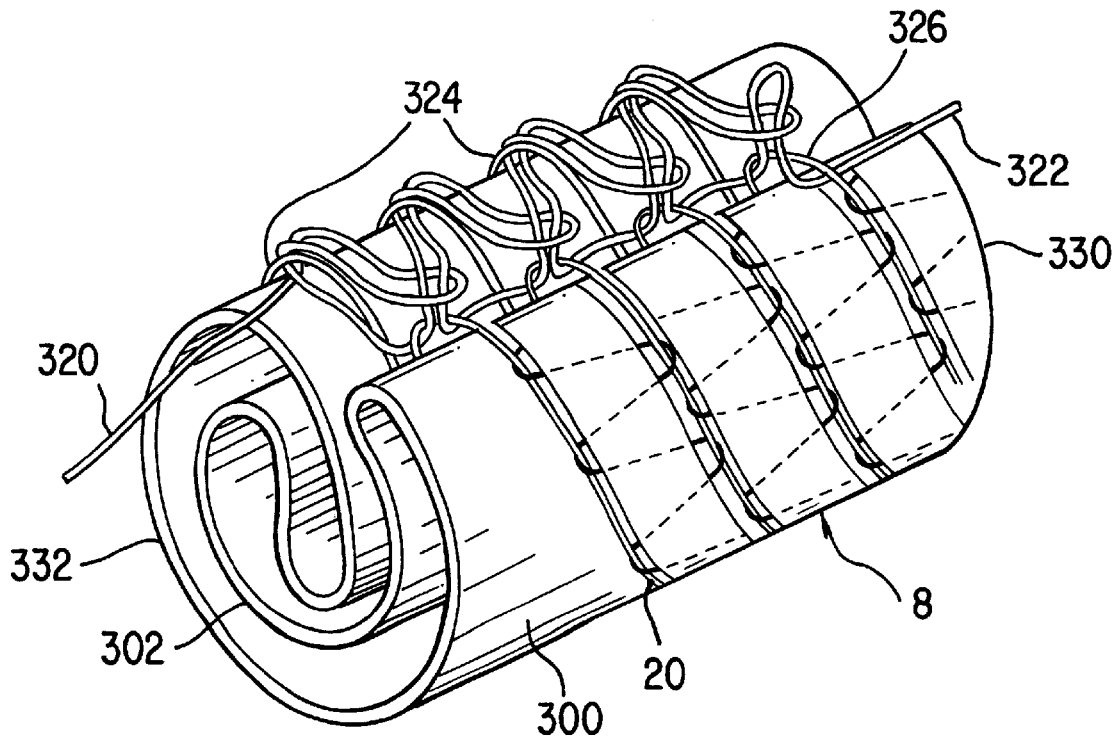
FIG. 1 is a diagrammatic perspective view of a folded stent-graft held in position by a tether line in a sack knot configuration in accordance with the principles of the present invention.

Referring to the drawings generally, wherein like numerals indicate like elements throughout the several drawings, and to FIG. 1 in particular, there is shown a diagrammatic perspective view of an exemplary stent-graft 300 folded and constrained by means of a stent tether or slip line configuration 308 (See FIG. 2) in accordance with the principles of the present invention. Although a particular stent-graft will be described, it should be understood that this description is for the purpose of presenting an example, and that other stent-graft constructions can be used. The stent fold line 302 configurations and deployment methods of the present invention, which are discussed in detail below with respect to FIGS. 1, 2, and 4A–C, may be employed with a variety of stent-graft configurations such as that illustrated in FIGS. 3A and 3B. The exemplary stent-graft configuration of FIGS. 3A and 3B is discussed first in order to shed light on the description of the deployment apparatus and methods of the present invention.

Figure 3A:
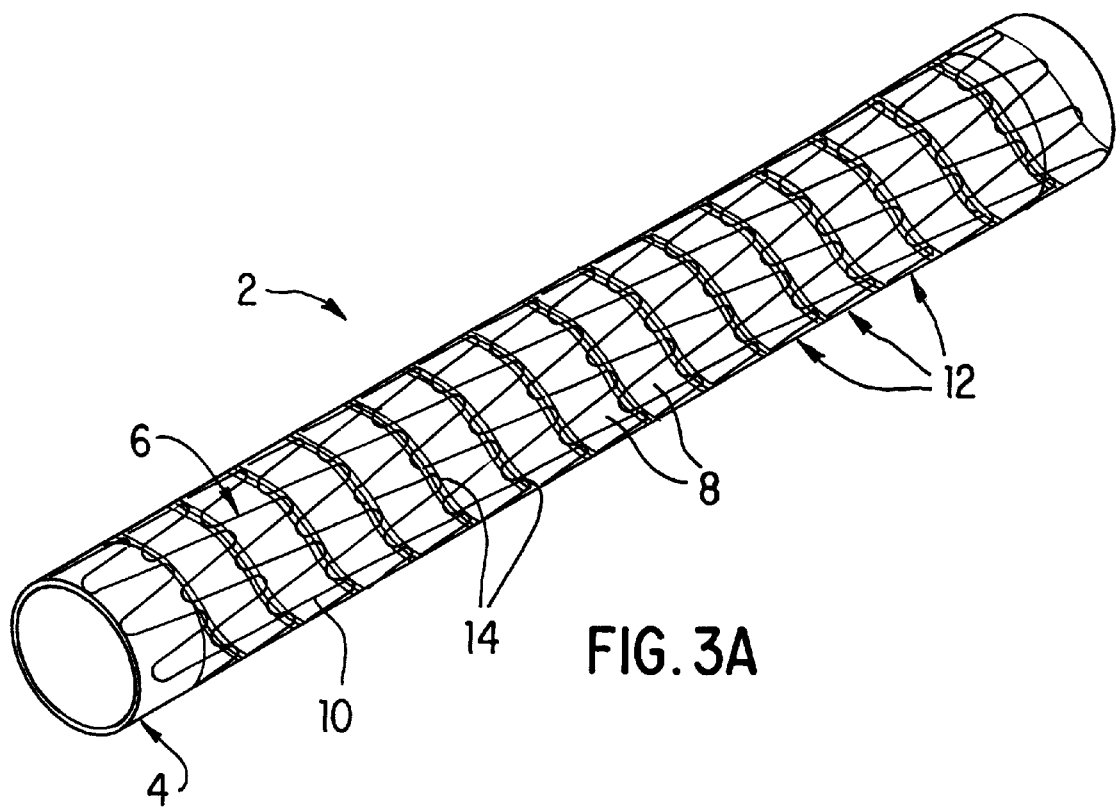
FIG. 3A is a perspective view of the stent-graft FIG. 1 in an unfolded state.
Figure 3B:
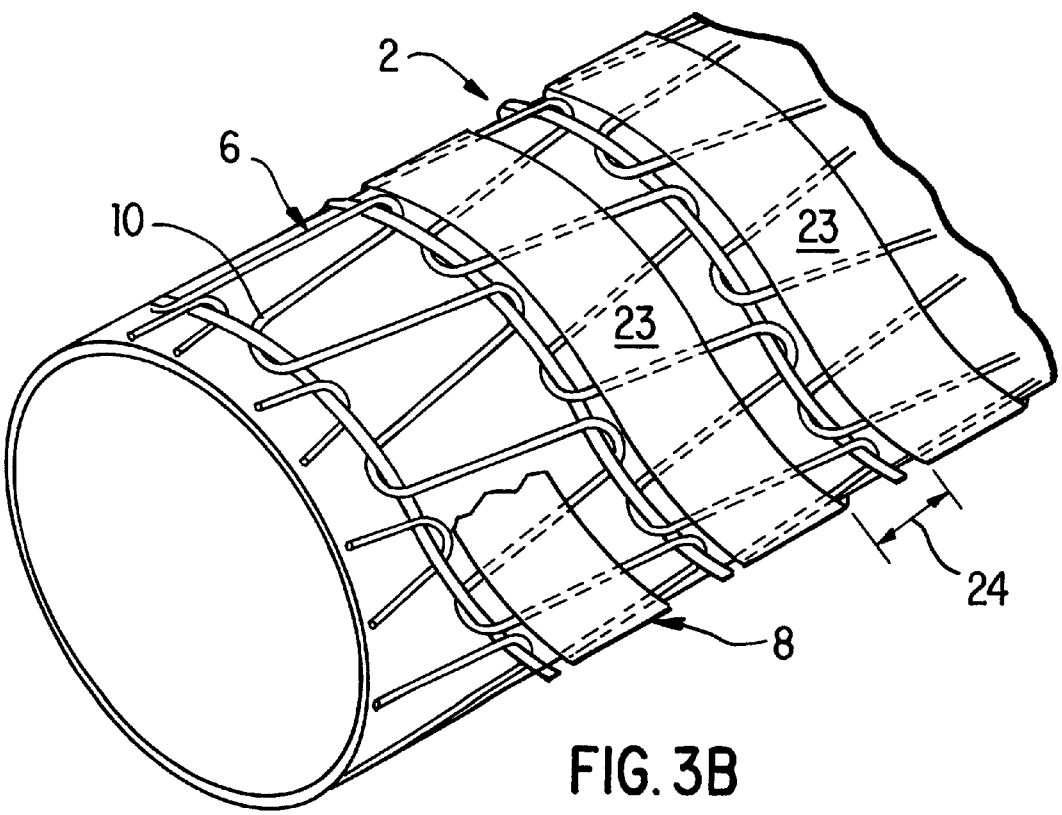
FIG. 3B is an enlarged perspective view of a mid-portion of the stent-graft of FIG. 3A.

FIG. 3A shows an expandable stent-graft 300. Expandable stent-graft 300 generally includes a thin-walled tube or graft member 4, an expandable stent member 6, and a coupling member 8 for coupling the stent and graft members together. Stent member 6, disposed between generally tubular graft member 4 and coupling member 8, provides a support structure for graft member 4 to minimize the likelihood of graft member 4 collapsing during use.

Expandable stent member 6 is generally cylindrical and comprises a helically arranged undulating member 10 having a plurality of helical turns 12 and preferably comprising nitinol wire, although other materials may be used, as described in detail below. Undulating helical member 10 forms a plurality of undulations 14 which are preferably aligned so that they are generally "in phase" with each other as shown in the drawings. A linking member 20 is provided to maintain the phased relationship of undulations 14 during compression and deployment as well as during bending of the stent member 6. As more clearly shown in the enlarged sectional view of FIG. 3B, linking member 20 is laced or interwoven between undulations in adjacent turns of helical member 10 and, thus, acquires a helical configuration as well. Linking member 20 preferably comprises a biocompatible polymeric or metallic material having sufficient flexibility to be readily folded upon itself.

Coupling member 8, which secures the stent member to the graft member 4, covers only a portion of the stent member 6. Alternatively, coupling member 8 can be described as preferably interconnecting less than entirely the inner or outer surface of stent member 6 to graft member 4 (e.g., it covers less than all of the outer surface of stent member 6 when graft member 4 is positioned inside stent member 6). With this construction, regions of the stent member do not interface with the coupling member when the stent-graft is an uncompressed state, for example. This is believed to advantageously reduce sheer stresses between the stent member and the coupling member when the stent-graft undergoes bending or compression, thereby reducing the risk of tearing the graft or coupling member or causing delamination between the stent and graft members.

Coupling member 8 preferably has a generally broad or flat surface for interfacing with the stent 6 and graft members 4, and is arranged in a helical configuration. This broad surface increases the potential bonding surface area between coupling member 8 and graft member 4 to enhance the structural integrity of the stent-graft. The increased bonding surface area also facilitates minimizing the thickness of the coupling member. It has been found that a coupling member 8 in the form of a generally flat ribbon or tape, as shown in the enlarged sectional view of FIG. 3B, provides preferable results.

In FIG. 3B, coupling member 8 is shown formed with multiple helical turns 23, each being spaced from the turns adjacent thereto, thereby forming coupling member-free stress relief zones 24 between adjacent turns. The coupling member also preferably is arranged to provide a generally uniform distribution of stress relief zones 24. In the illustrated embodiment, coupling member 8 is helically wound around stent member 6 with its helical turns 23 aligned with the stent member turns 12.

Coupling member 8 also preferably covers a substantial portion of each undulation 14 so as to minimize the likelihood of stent member 6 lifting away from graft member 4. As shown, the coupling member may be constructed with a constant width and arranged with uniform spacing between the turns. Coupling members having widths of 0.025, 0.050, and 0.075 inches have been applied to the illustrated stent member having a peak-to-peak undulation amplitude of about 0.075 inch with suitable results. However, it has been found that as the coupling member band width increases, the stent-graft flexibility generally is diminished. It is believed that a coupling member width of about one-fourth to three-fourths the amplitude of undulations 14, measured peak-to-peak, is preferred (and more preferably one-third to two-thirds) to optimize flexibility. Coupling member 8 (or separate pieces thereof) preferably also surrounds the terminal end portions 16 and 18 of stent-graft 2 to secure the terminal portions of graft member 4 to the support the structure formed by stent member 6.

It should be noted that the above-described stent-graft configuration of FIGS. 3A and 3B is only exemplary. Other stent-graft configurations and constructions can be used with the present invention, such as those disclosed in PCT Publication WO 95/26695, which is hereby incorporated by reference herein in its entirety.

The scope of materials suitable for the stent and graft members and the linking member described above as well as deployment mechanisms will be discussed in detail below.

Stent Materials

The stent member is constructed of a reasonably high strength material, i.e., one which is resistant to plastic deformation when stressed. Preferably, the stent member comprises a wire which is helically wound around a mandrel having pins arranged thereon so that the helical turns and undulations can be formed simultaneously. Other constructions also may be used. For example, an appropriate shape may be formed from a flat stock and wound into a cylinder or a length of tubing formed into an appropriate shape.

In order to minimize the wall thickness of the stent-graft, the stent material should have a high strength-to-volume ratio. Designs as depicted herein provide stents which may be longer in length than conventional designs. Additionally, the designs do not suffer from a tendency to twist (or helically unwind) or to shorten as the stent-graft is deployed. As will be discussed below, materials suitable in these stents and meeting these criteria include various metals and some polymers.

A percutaneously delivered stent-graft must expand from a reduced diameter, necessary for delivery, to a larger deployed diameter. The diameters of these devices obviously vary with the size of the body lumen into which they are placed. For instance, the stents may range in size from 2.0 mm in diameter for neurological applications to 40 mm in diameter for placement in the aorta. Typically, expansion ratios of 2:1 or more are required. These stents are capable of expansion ratios of up to 5:1 for larger diameter stents. The thickness of the stent materials obviously varies with the size (or diameter) of the stent and the ultimate required yield strength of the folded stent. These values are further dependent upon the selected materials of construction. Wire used in these variations are typically of stronger alloys, e.g., nitinol and stronger spring stainless steels, and have diameters of about 0.002 inches to 0.005 inches. For the larger stents, the appropriate diameter for the stent wire may be somewhat larger, e.g., 0.005 to 0.020 inches. For flat stock metallic stents, thicknesses of about 0.002 inches to 0.005 inches is usually sufficient. For the larger stents, the appropriate thickness for the stent flat stock may be somewhat thicker, e.g., 0.005 to 0.020 inches.

The stent-graft is fabricated in the expanded configuration. In order to reduce its diameter for delivery the stent-graft would be folded along its length, similar to the way in which a PCTA balloon would be folded. It is desirable, when using super-elastic alloys which also have temperature-memory characteristics, to reduce the diameter of the stent at a temperature below the transition-temperature of the alloys. Often the phase of the alloy at the lower temperature is somewhat more workable and easily formed. The temperature of deployment is desirably above the transition temperature to allow use of the super-elastic properties of the alloy.

There are a variety of disclosures in which super-elastic alloys such as nitinol are used in stents. See, U.S. Pat. Nos. 4,503,569, to Dotter; 4,512,338, to Balko et al.; 4,990,155, to Wilkoff; 5,037,427, to Harada, et al.; 5,147,370, to MacNamara et al.; 5,211,658, to Clouse; and 5,221,261, to Termin et al. None of these references suggest a device having discrete, individual, energy-storing torsional members.

Jervis, in U.S. Pat. Nos. 4,665,906 and 5,067,957, describes the use of shape memory alloys having stress-induced martensite properties in medical devices which are implantable or, at least, introduced into the human body.

A variety of materials variously metallic, super elastic alloys, and preferably nitinol, are suitable for use in these stents. Primary requirements of the materials are that they be suitably springy even when fashioned into very thin sheets or small diameter wires. Various stainless steels which have been physically, chemically, and otherwise treated to produce high springiness are suitable as are other metal alloys such as cobalt chrome alloys (e.g., ELGILOY®), platinum/tungsten alloys, and especially the nickel-titanium alloys generically known as "nitinol".

Nitinol is especially preferred because of its "super-elastic" or "pseudo-elastic" shape recovery properties, i.e., the ability to withstand a significant amount of bending and flexing and yet return to its original form without deformation. These metals are characterized by their ability to be transformed from an austenitic crystal structure to a stress-induced martensitic structure at certain temperatures, and to return elastically to the austenitic shape when the stress is released. These alternating crystalline structures provide the alloy with its super-elastic properties. These alloys are well known but are described in U.S. Pat. Nos. 3,174,851, 3,351,463, and 3,753,700. Typically, nitinol will be nominally 50.6% (±0.2%) Ni with the remainder Ti. Commercially available nitinol materials usually will be sequentially mixed, cast, formed, and separately cold-worked to 30–40%, annealed, and stretched. Nominal ultimate yield strength values for commercial nitinol are in the range of 30 psi and for Young's modulus are about 700 Kbar. The '700 patent describes an alloy containing a higher iron content and consequently has a higher modulus than the Ni—Ti alloys.

Nitinol is further suitable because it has a relatively high strength to volume ratio. This allows the torsion members to be shorter than for less elastic metals. The flexibility of the stent-graft is largely dictated by the length of the torsion segments and/or torsion arms. The shorter the pitch of the device, the more flexible the stent-graft structure can be made. Materials other than nitinol are suitable. Spring tempered stainless steels and cobalt-chromium alloys such as ELGILOY® are also suitable as are a wide variety of other known "super-elastic" alloys.

Although nitinol is preferred in this service because of its physical properties and its significant history in implantable medical devices, we also consider it also to be useful in a stent because of its overall suitability with magnetic resonance imaging (MRI) technology. Many other alloys, particularly those based on iron, are an anathema to the practice of MRI causing exceptionally poor images in the region of the alloy implant. Nitinol does not cause such problems.

Other materials suitable as the stent include certain polymeric materials, particularly engineering plastics such as thermotropic liquid crystal polymers ("LCP's"). These polymers are high molecular weight materials which can exist in a so-called "liquid crystalline state" where the material has some of the properties of a liquid (in that it can flow) but retains the long range molecular order of a crystal. The term "thermotropic" refers to the class of LCP's which are formed by temperature adjustment. LCP's may be prepared from monomers such as p,p'-dihydroxy-polynuclear-aromatics or dicarboxy-polynuclear-aromatics. The LCP's are easily formed and retain the necessary interpolymer attraction at room temperature to act as high strength plastic artifacts as are needed as a foldable stent. They are particularly suitable when augmented or filled with fibers such as those of the metals or alloys discussed below. It is to be noted that the fibers need not be linear but may have some preforming such as corrugations which add to the physical torsion enhancing abilities of the composite.

Linking Member Materials

Flexible link 20, which is slidably disposed between adjacent turns of the helix may be of any appropriate filamentary material which is blood compatible or biocompatible and sufficiently flexible to allow the stent to flex and not deform the stent upon folding. Although the linkage may be a single or multiple strand wire (platinum, platinum/tungsten, gold, palladium, tantalum, stainless steel, etc.), the use of polymeric biocompatible filaments is preferable. Synthetic polymers such as polyethylene, polypropylene, polyurethane, polyglycolic acid, polyesters, polyamides, their mixtures, blends and copolymers are suitable; preferred of this class are polyesters such as polyethylene terephthalate including DACRON® and MYLAR® and polyaramids such as KEVLAR®, polyfluorocarbons such as polytetrafluoroethylene with and without copolymerized hexafluoropropylene (TEFLON® or GORE-TEX®), and porous or nonporous polyurethanes. Natural materials or materials based on natural sources such as collagen may also be used.

Graft Member Materials

The tubular component or graft member of the stent-graft may be made up of any material which is suitable for use as a graft in the chosen body lumen. Many graft materials are known, particularly known are those used as vascular graft materials. For instance, natural materials such as collagen may be introduced onto the inner surface of the stent and fastened into place. Desirable collagen-based materials include those described in U.S. Pat. No. 5,162,430, to Rhee et al, and WO 94/01483 (PCT/US93/06292), the entirety of which are incorporated by reference. Synthetic polymers such as polyethylene, polypropylene, polyurethane, polyglycolic acid, polyesters, polyamides, their mixtures, blends and copolymers are suitable; preferred of this class are polyesters such as polyethylene terephthalate including DACRON® and MYLAR® and polyaramids such as KEVLAR®, polyfluorocarbons such as polytetrafluoroethylene (PTFE) with and without copolymerized hexafluoropropylene (TEFLON® or GORE-TEX®), and porous or nonporous polyurethanes. Especially preferred are the expanded fluorocarbon polymers (especially PTFE) materials described in British. Pat. Nos. 1,355,373, 1,506,432, or 1,506,432 or in U.S. Pat. Nos. 3,953,566, 4,187,390, or 5,276,276, the entirety of which are incorporated by reference.

Included in the class of preferred fluoropolymers are polytetrafluoroethylene (PTFE), fluorinated ethylene propylene (FEP), copolymers of tetrafluoroethylene (TFE) and perfluoro (propyl vinyl ether) (PFA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinyfluoride (PVF). Especially preferred, because of its widespread use in vascular prostheses, is expanded PTFE.

In addition, one or more radio-opaque metallic fibers, such as gold, platinum, platinum-tungsten, palladium, platinum-iridium, rhodium, tantalum, or alloys or composites of these metals like may be incorporated into the device, particularly, into the graft, to allow fluoroscopic visualization of the device.

The tubular component may also be reinforced using a network of small diameter fibers. The fibers may be random, braided, knitted, or woven. The fibers may be imbedded in the tubular component, may be placed in a separate layer coaxial with the tubular component, or may be used in a combination of the two.

A preferred material for the graft and coupling members is porous expanded polytetrafluorethylene. An FEP coating is one preferred adhesive that is provided on one side of the coupling member.

Manufacture of the Stent-Graft

The following example is provided for purposes of illustrating a preferred method of manufacturing a stent-graft such as the one shown in FIGS. 3A and 3B. It should be noted, however, that this example is not intended to limit the invention.

The stent member wire is helically wound around a mandrel having pins positioned thereon so that the helical structure and undulations can be formed simultaneously. While still on the mandrel, the stent member is heated to about 460° F. for about 20 minutes so that it retains its shape.

Wire sizes and materials may vary widely depending on the application. The following is an example construction for a stent-graft designed to accommodate a 6 mm diameter vessel lumen. The stent member comprises a nitinol wire (50.8 atomic % Ni) having a diameter of about 0.007 inch. In this example case, the wire is formed to have sinusoidal undulations, each having an amplitude measured peak-to-peak of about 0.100 inch and the helix is formed with a pitch of about 10 windings per inch. The inner diameter of the helix (when unconstrained) is about 6.8 mm. The linking member can be arranged as shown in the drawings and may have a diameter of about 0.006 inch.

In this example, the graft member is porous expanded polytetrafluorethylene (PTFE), while the coupling member is expanded PTFE coated with FEP. The coupling member is in the form of a flat ribbon (as shown in the illustrative embodiments) that is positioned around the stent and graft members as shown in FIG. 3B. The side of the coupling member or ribbon that is FEP coated faces the graft member to secure it to the graft member. The intermediate stent-graft construction is heated to allow the materials of the ribbon and graft member to merge and self-bind as will be described in more detail below.

The FEP-coated porous expanded PTFE film used to form the ribbon shaped coupling member preferably is made by a process which comprises the steps of:

(a) contacting a porous PTFE film with another layer which is preferably a film of FEP or alternatively of another thermoplastic polymer;

(b) heating the composition obtained in step (a) to a temperature above the melting point of the thermoplastic polymer;

(c) stretching the heated composition of step (b) while maintaining the temperature above the melting point of the thermoplastic polymer; and (d) cooling the product of step (c).

In addition to FEP, other thermoplastic polymers including thermoplastic fluoropolymers may also be used to make this coated film. The adhesive coating on the porous expanded PTFE film may be either continuous (non-porous) or discontinuous (porous) depending primarily on the amount and rate of stretching, the temperature during stretching, and the thickness of the adhesive prior to stretching.

The thin wall expanded PTFE graft used to construct this example is of about 0.1 mm (0.004 in) thickness and has a density of about 0.5 g/cc. The microstructure of the porous expanded PTFE contains fibrils of about 25 micron length. A 3 cm length of this graft material is placed on a mandrel the same diameter as the inner diameter of the graft. The nitinol stent member having about a 3 cm length is then carefully fitted over the center of the thin wall graft.

The stent-member was then provided with a ribbon shaped coupling member comprised of the FEP coated film as described above. The coupling member was helically wrapped around the exterior surface of the stent-member as shown in FIG. 3B. The ribbon shaped coupling member was oriented so that its FEP-coated side faced inward and contacted the exterior surface of the stent-member. This ribbon surface was exposed to the outward facing surface of the thin wall graft member exposed through the openings in the stent member. The uniaxially-oriented fibrils of the microstructure of the helically-wrapped ribbon were helically-oriented about the exterior stent surface.

The mandrel assembly was placed into an oven set at 315° C. for a period of 15 minutes after which the film-wrapped mandrel was removed from the oven and allowed to cool. Following cooling to approximately ambient temperature, the mandrel was removed from the resultant stent-graft. The amount of heat applied was adequate to melt the FEP-coating on the porous expanded PTFE film and thereby cause the graft and coupling members to adhere to each other. Thus, the graft member was adhesively bonded to the inner surface of helically-wrapped coupling member 8 through the openings between the adjacent wires of the stent member. The combined thickness of the luminal and exterior coverings (graft and coupling members) and the stent member was about 0.4 mm.

The stent-graft was then folded in order to prepare it for delivery. To accomplish this a stainless steel wire which was at least about two inches longer than the stent-graft was inserted through the lumen of the stent-graft. The stent-graft was flattened and the stainless steel wire positioned at one end of the stent-graft. A second stainless steel wire of about the same length was placed on the outer surface of the stent-graft adjacent to the first stainless steel wire. The wires were then mounted together into a fixture, tensioned and then rotated, thereby folding the stent-graft. As the stent-graft rotates it is pressed into a "C" shaped elongated stainless steel clip in order to force it to roll upon itself. The folded stent-graft is then advanced along the wire out of the clip into a glass capture tube. A removable tether line, which is used to constrain the stent-graft in the rolled configuration for delivery is applied to the stent-graft at this point by gradually advancing the stent-graft out of the capture tube and lacing the tether line through the stent-graft structure. After this step is completed, the stent-graft is pulled off of the first wire and transferred onto the distal end of the catheter shaft or tubing for delivery.

Prior to folding, the stent-graft was cooled to about −30° C. so that the nitinol was fully martensitic and, thus, malleable. This is done to allow the stent-graft to be more easily folded. Cooling is accomplished by spray soaking the graft with chilled gas such as tetrafluroethane. Micro-Dust™ dry circuit duster manufactured by MicroCare Corporation (Conn) provides suitable results. The spray canister was held upside down to discharge the fluid as a liquid onto the stent-graft.

Deployment of the Stent-Graft

The stent-graft may be delivered percutaneously, typically through the vasculature, after having been folded to a reduced diameter. Once reaching the intended delivery site, it may be expanded to form a lining on the vessel wall.

When a stent-graft having torsion members, as described above, is folded, crushed, or otherwise collapsed, mechanical energy is stored in torsion in those members. In this loaded state, the torsion members have a torque exerted about them and consequently have a tendency to untwist. Collectively, the torque exerted by the torsion members as folded down to a reduced diameter must be restrained from springing open. The stent-member preferably has at least one torsion member per fold. The stent-graft is folded along its longitudinal axis and restrained from springing open. As is apparent from the foregoing, the stent-graft is a self-expanding stent-graft. The stent-graft is then deployed by removing the restraining mechanism, thus allowing the torsion members to spring open against the vessel wall. The attending physician will select an appropriately sized stent-graft. Typically, the stent-graft will be selected to have an expanded diameter of up to about 10% greater than the diameter of the lumen at the deployment site.

Figure 4A:
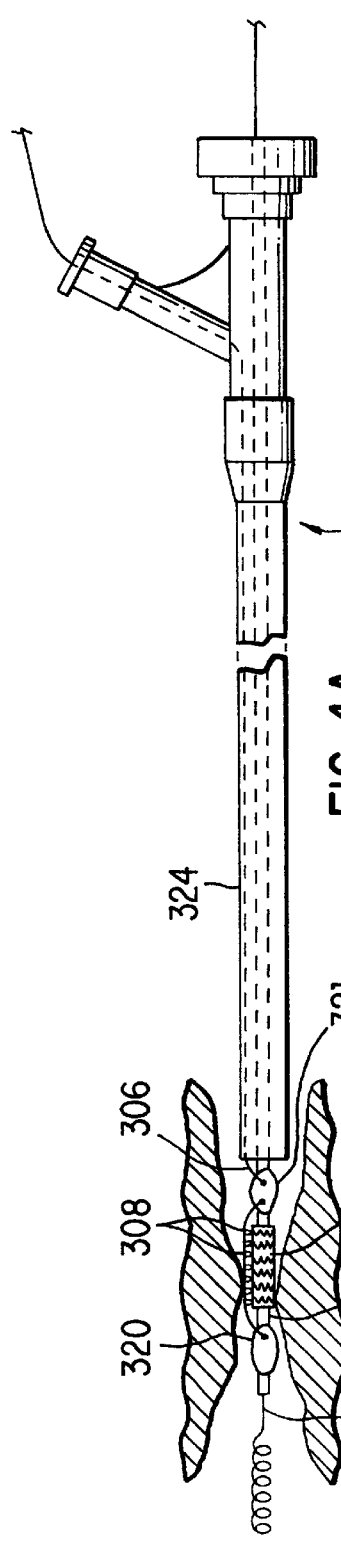
FIGS. 4A, 4B, and 4C diagrammatically show a method of deploying a stent-graft according to the present invention for deploying the stent graft shown in FIG. 1
Figure 4B:
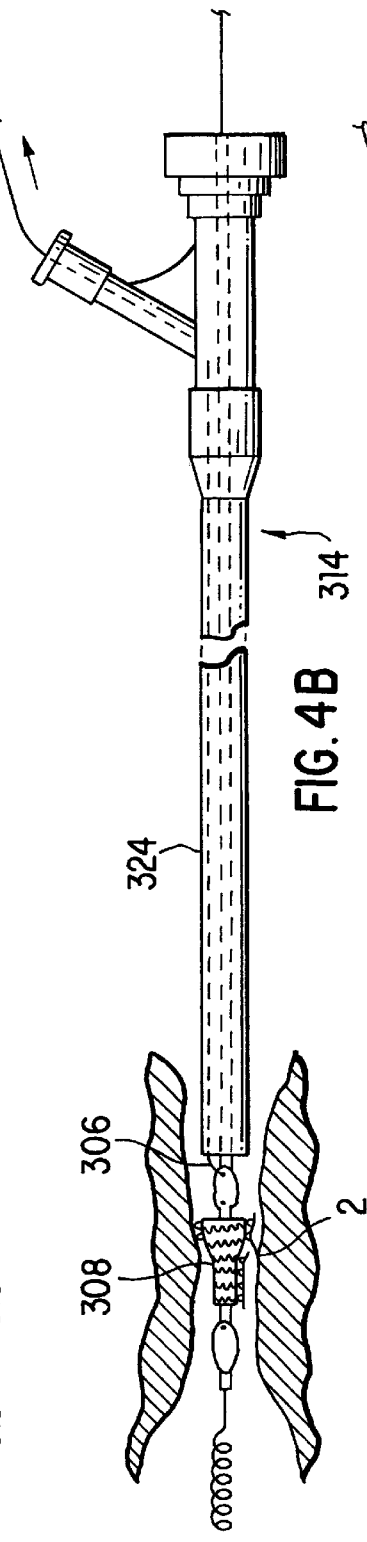
Figure 4C:
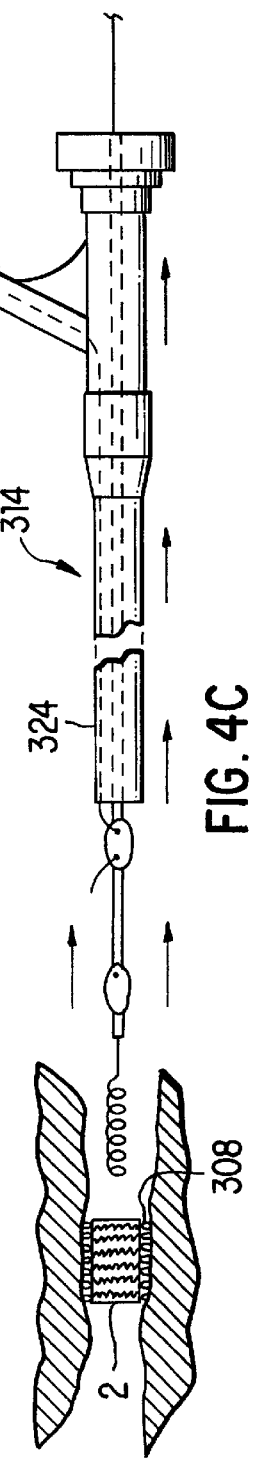

FIGS. 4A–C diagrammatically show a procedure for deploying a stent-graft assembly, constructed according to the present invention, using a percutaneous dual-lumen catheter assembly 314. Catheter assembly 314 includes a catheter or delivery member shaft portion 325, a hub portion 327, and a tip portion 312. Extending coaxially within shaft portion 325 are two parallel channels, a guidewire channel 331 and a tether line channel 329. Shaft portion 325 has a distal end portion 310. Extending through guidewire channel 331 and beyond distal end portion 310 is a guidewire tube 318. Running through and extending distally beyond the end of guidewire tube 318 is guidewire 319. Axially mounted on the distal end of guidewire tube 318 are a proximal barrier 321 and a distal barrier 320.

Referring particularly to FIG. 4A, catheter assembly 314 has been inserted into a selected site within a body lumen 350. A stent-graft, such as stent-graft 300 described in conjunction with FIGS. 3A and B, is folded about guidewire tube 318 and is held axially in place prior to deployment between distal and proximal barriers 320, 321. Tether wire 306 extends through loops 308 and through tether line channel 329 and hub portion 327 of catheter 314 to outside the body. Tether wire 306 may be outside proximal barrier 321 or extend therethrough as shown in FIG. 4A.

Deployment of stent-graft 300 is accomplished by actuating or pulling tether wire 306 in the direction of arrow 370, as shown in FIG. 4B. FIG. 4B shows partial removal of tether wire 306 from loops 308 to partially deploy and expand the stent-graft 300 onto the selected site. With this configuration, stent-graft 300 can be described as opening or deploying in a hub-to-tip direction with respect to catheter 314 and in a proximal-to-distal direction with respect to the stent-graft itself (i.e., the end of the stent-graft proximate to distal end 310 of shaft portion 325 opens first). FIG. 4C shows tether wire 306, the loops thereof which have been completely retracted from the interior of stent-graft 300 which is now in its fully unfolded, deployed state within lumen 350.

The hub-to-tip or proximal-to-distal deployment method of the present invention, described above with respect to FIGS. 4A–C, is accomplished in part by the manner in which the tether or slip line is configured to the stent-graft. FIGS. 1 and 2 show a preferred embodiment of the tether line configuration of the present invention. In FIG. 1, stent-graft 300 is shown having a proximal portion 330 and a distal portion 332. When stent-graft 300 is used for its intended purpose in conjunction with a deployment means, such as the catheter assembly 314 illustrated in FIGS. 4A–C, proximal portion 330 is positioned proximate to and associated with distal end 310 of catheter assembly 314. As such, distal portion 332 of stent-graft 300 is positioned proximate to and associated with the tip portion 312 of catheter assembly 314.

Stent-graft 300 is held in position by a tether or slip line 306 in a sack knot configuration in accordance with the present invention. FIG. 1 shows the use of a single stent fold 302. The fixed end portion 306' of slip line 306 is associated with distal end 332 of stent-graft 300 and a row of eyelets 324. Conversely, the release end 322 of slip line 306 is associated with proximal end 330 of stent-graft 300. The eyelets are preferably formed by pulling local portions of linking member 20 away from the fold line, threading slip line 306 therethrough, and then releasing the respective portion of linking member 20. The eyelets may then be tied or otherwise fixed to the stent.

FIG. 2 shows the stent fold line 306" having the herringbone pattern of the "sack knot" configuration used to close the fold in stent 300 in FIG. 1. This knot is the one used to hold, for example, burlap sacks of feed grain closed prior to use which allow ease of opening when the sack is to be opened. Slip line 306 has a fixed end 306' and a release end 322. Loops of slip line 306 pass through the eyelets 324 on the side of the stent fold associated with the fixed end 306'. It should also be noted that the fixed end 306' is not typically tied to stent 300 so as to allow removal of the slip line after deployment. Additionally, the eyelets 324 and 326 are desirable but optional. The eyelets 324 and 326 may be wire or polymeric thread or the like tied to the stent structure at the edge of the stent fold. Alternatively, eyelets 324 and 326 may be formed from linking member 20, as discussed above, to form the loops through which slip line 306 passes. In a further configuration, slip line 306 may be woven into the stent structure, for example, into undulations 14 as shown in FIG. 3A.

Release end 322 of slip line 306 is positioned so that, when the stent-graft deployment or release mechanism (not shown) is associated with stent-graft 300, it is in the vicinity of the proximal portion 330 of stent-graft 300. Thus, when release end 322 is pulled in the direction of arrow 334, the stent-graft 300 unfolds from the proximal end 330 to the distal end 332 (see FIG. 4B).

Alternatively, the loops of the slip line may pass through eyelets 326 on the side of the stent fold associated with release end 322, as depicted in phantom in FIG. 2. With this latter arrangement, release end 322 is pulled in the direction of arrow 336, and stent-graft 300 unfolds in the opposite direction, from distal end 332 towards proximal end 330. However, this distal-to-proximal unfolding arrangement, due to the extra folded-back length of tether line leading to release end 322, is more likely to cause the tether line to become entangled upon deployment of the stent-graft.

The preferred proximal-to-distal deployment arrangement eliminates the extra folded-back length of the tether line leading to the release end and, thus, may reduce the likelihood of snagging between the slip line and stent member. This arrangement also provides less fluid flow resistance when the stent-graft is deployed against the flow of blood (i.e., from a downstream to upstream direction), which in turn improves positioning accuracy during deployment, particularly in the course of an aortic procedure. Other means, within the scope of the invention, are contemplated to be employed to hold the stent device in an unfolded or constricted configuration and to activate the proximal-to-distal deployment arrangement of the present invention. These means include adhesive tape having a perforation which facilitates easy tear-away, a Velcro strip that can be peeled away from a stent device, a zipper or clasp mechanism, or any other suitable interlocking-type mechanism having a pull actuator.

The disclosures of any publications, patents and published patent applications referred to in this application are hereby incorporated by reference.

The above is a detailed description of a particular embodiment of the invention. The full scope of the invention is set out in the claims that follow and their equivalents. Accordingly, the claims and specification should not be construed to unduly narrow the full scope of protection to which the invention is entitled.

What is claimed is:

1. An apparatus comprising:
a stent with first and second ends, said stent having a folded configuration and an unfolded substantially tubular configuration;
a graft coupled to said stent; and
a line positioned external to said stent temporarily maintaining said stent in said folded configuration and arranged to be released as a result of an axial pulling force so that said stent may progressively expand to achieve said unfolded configuration.

2. The apparatus of claim 1 wherein said line is arranged in a sack knot configuration.

3. The apparatus of claim 2 wherein said sack knot configuration has a herringbone pattern.

4. The apparatus of claim 1 further including a deployment device.

5. The apparatus of claim 1, wherein said graft is coaxially coupled to said stent.

6. The apparatus of claim 4 wherein said stent has at least one fold substantially aligned with said deployment device, when in said folded configuration.

7. The apparatus of claim 1 wherein said stent comprises a helical member and a linking member, said helical member having multiple helical turns in phase with one another.

8. The device of claim 1, wherein said graft comprises a fluoropolymer.

9. The device according to claim 7, wherein a helically disposed coupling member covers a portion of said helical member.

10. The apparatus of claim 1, wherein said stent has a proximal portion and a distal portion, and wherein said stent progressively expands in a direction from said proximal portion to said distal portion.

11. A deployment device comprising:
a substantially tubular stent having a constricted configuration and an expanded configuration, said stent comprising a helical member having multiple helical turns which are in phase with one another;
a graft attached to said stent; and
a line positioned external to said stent disposed along said stent to hold said stent in its constricted configuration, wherein when said line is pulled in an axial direction, said stent progressively expands from its constricted configuration.

12. The deployment device of claim 11 wherein said constricted configured stent is associated with a shaft of a catheter.

13. The device of claim 10, wherein said graft is coaxially coupled to said stent.

14. The device of claim 11, wherein said graft comprises a fluoropolymer.

15. The device according to claim 11, wherein a helically disposed coupling member covers a portion of said helical member.

16. An apparatus comprising:
a stent having first and second ends, a helical member and a linking member, and a helically disposed coupling member covering a portion of said helical member, said helical member having multiple helical turns in phase with one another, said stent having a folded configuration and an unfolded substantially tubular configuration; and
a line positioned external to said stent temporarily maintaining said stent in said folded configuration and arranged to be released as a result of an axial pulling force so that said stent may progressively expand to achieve said unfolded configuration.

17. A deployment device comprising:
a substantially tubular stent having a constricted configuration and an expanded configuration, said stent comprising a helical member having multiple helical turns which are in phase with one another, wherein a helically disposed coupling member covers a portion of said helical member; and
a line positioned external to said stent disposed along said stent to hold said stent in its constricted configuration, wherein when said line is pulled in an axial direction, said stent progressively expands from its constricted configuration.

18. A medical device comprising:
an implant having a proximal portion and a distal portion and a longitudinally extending fold line, said implant including a stent and a graft; and
a line releasably coupled to said fold line to hold said implant in a folded state, said line being arranged to be released causing said implant to progressively expand to a deployed configuration.

19. Medical device comprising:
a stent having a proximal portion and a distal portion;
a graft member coupled to said stent;
a linking member coupled to said stent; and
a line releasably coupled to said linking member to hold said stent in a folded state, said line being arranged to be released from said linking member and causing said stent to progressively expand to a deployed configuration.

20. A medical device comprising:
an expandable implant having a proximal portion, a distal portion, and plurality of openings, said implant comprising a stent and a graft; and
a line releasably coupled to said implant to hold said implant in a folded state, wherein said line passes through said plurality of openings, said line being arranged to be released causing said implant to progressively expand to a deployed configuration.

* * * * *